United States Patent [19]

Boelens et al.

[11] 4,442,025

[45] Apr. 10, 1984

[54] PERFUME COMPOSITIONS AND PERFUMED ARTICLES CONTAINING ESTERS OF SUBSTITUTED BICYCLO [2.2.1]HEPTENE- AND HEPTINE-CARBOXYLIC ACIDS AS PERFUME BASE

[75] Inventors: Harmannus Boelens; Antonius J. A. van der Weerdt; Theodorus G. M. Hesp, all of Huizen, Netherlands

[73] Assignee: Naarden International, N.V., Naarden-Bussum, Netherlands

[21] Appl. No.: 267,644

[22] Filed: May 27, 1981

[30] Foreign Application Priority Data

May 28, 1980 [NL] Netherlands ............... 8003068

[51] Int. Cl.$^3$ .................. A61K 7/46; C11B 9/00
[52] U.S. Cl. ................ 252/522 R; 252/174.11; 424/65; 424/69; 424/70
[58] Field of Search ............ 252/522 R, 174.11; 560/120; 424/65, 69, 70

[56] References Cited

U.S. PATENT DOCUMENTS

| 4,053,657 | 10/1977 | Schreiber et al. | 426/538 |
|---|---|---|---|
| 4,319,036 | 3/1982 | Klemarczyk | 252/522 R |

FOREIGN PATENT DOCUMENTS

| 2743 | 12/1977 | European Pat. Off. . |
| 2403328 | 10/1977 | France . |
| 277216 | 4/1962 | Netherlands . |
| 7014660 | 4/1971 | Netherlands . |
| 7603354 | 3/1976 | Netherlands . |
| 7605914 | 6/1976 | Netherlands . |
| 7605913 | 6/1976 | Netherlands . |
| 7810966 | 5/1978 | Netherlands . |

OTHER PUBLICATIONS

Monatsh. Chem. 107, 387–394, 945–948 (1976).
Monatsh. Chem. 109, 3–9 (1978).
Kurt Alder und Wolfgang Roth, Syntheses und Konfiguration der Camphenilan- und der Isocamphenilansaure Sowie der aus Ihnen Abgelcitetch Alkohole.
Alder, Hartmann und Roth, Synthesen in der Bicyclo-[1.2.2]-heptan-Reihe, Darstellung von Nortricyclen-carbonsauren.
Chemical Abstracts, 88:458, 12013p, (1978).

Primary Examiner—John F. Niebling
Attorney, Agent, or Firm—Brumbaugh, Graves, Donohue & Raymond

[57] ABSTRACT

Use of one or more esters of methyl substituted bicyclo [2.2.1]heptane- and heptene-carboxylic esters with formula 1a and 1b, in which the dotted line is a single or double bond, $R_1$ represents a hydrogen atom or methyl group and $R_2$ represents an alkyl or alkenyl group having 1–4 carbon atoms as a perfume component in perfume compositions and in imparting perfume notes to articles, for example, soaps, cleaning preparations, cosmetic preparations.

8 Claims, No Drawings

PERFUME COMPOSITIONS AND PERFUMED ARTICLES CONTAINING ESTERS OF SUBSTITUTED BICYCLO [2.2.1]HEPTANE- AND HEPTENE-CARBOXYLIC ACIDS AS PERFUME BASE

The invention relates to perfume compositions containing esters of substituted bicyclo[2.2.1]heptane- and heptene-carboxylic acids as perfume base and to articles perfumed with these compounds.

There is a continuous interest for the preparation and application of synthetic fragrances because these fragrances can always be prepared in the quantity desired and with uniform quality, this contrary to naturally occurring substances. Especially there is a demand for synthetical fragrances having a natural odor. Moreover, for some applications like perfuming of modern detergents a high chemical stability is required.

It was found that esters of methyl-substituted bicy]2.2.1]heptane- and -heptene-carboxylic acids having the following structures according to formula 1a and/or 1b:

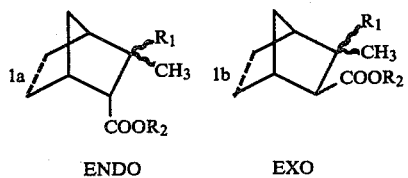

ENDO        EXO in which the dotted line is a carbon-carbon single or double bond, $R_1$ is a hydrogen atom or methyl group and $R_2$ is an alkyl- or alkenyl group having 1-4 carbon atoms are valuable fragrances having a fresh and very natural odor, strongly resembling conifers odor with spicy and sometimes minty and/or fruity notes.

The esters according to the invention may have the endo- or exo-configuration, respectively represented by formula 1a and 1b. Moreover when $R_1$ is a hydrogen atom, each of the formulae 1a and 1b represents an epimeric pair wherein the remaining methyl group have the cis- or trans-position in respect to the ester group. This epimerism is indicated in the formulae by the wavy lines.

Several fragrances having a bicyclo[2.2.1]heptane skeleton are known from the prior art. For instance U.S. Pat. No. 4,053,657 mentions many compounds having such a structure and a great variety of odors. However, none of these compounds do have a bicyclo[2.2.1]heptane carboxyl-unit so that these compounds strongly differ in chemical way from the compounds according to the invention.

On the other hand some methyl esters of the compounds according to the invention are known as such. For instance the methyl esters of endo- and exo-3.3-dimethyl-bicyclo[2.2.1]heptane-2-carboxylic acid (in the literature often indicated as camphenic acid respectively isocamphenic acid) are described in Monatsh. Chem. 107 (1976) 945-8 and 109 (1978) 3-9 as compounds which as well as the corresponding acids could be used as starting compounds for the synthesis of drugs and fragrances. However, nothing is mentioned about the possible fragrance properties of the compounds themselves. Further the above mentioned esters as well as the methyl esters of endo- and exo-6.6-dimethyl-bicyclo[2.2.1]hept-2-ene-carboxylic acid are mentioned in Chem. Ber. 90 (1957) 1830–37 also without any indication of olfactory properties.

In Dutch patent application 76,05914 laid open for public inspection it is described that monoesters, derived of methyl- and dimethyl-bicyclo[2.2.1]heptane and -heptene-carboxylic acids and alkyleneglycols or dialkyleneglycols do have a physiological cooling effect when these compounds are brought into contact with internal or external surface tissues of the body (skin, mucous membranes). However, there is nothing mentioned about the odor and possible fragrance properties of these compounds.

Further it is described in Dutch patent application 78,10966 that both 3.3-dimethyl-bicyclo[2.2.1]heptane-carboxylic acids are fragrances having a somewhat acidic odor reminiscent cistus oil and olibanum. However, it is not deducable from this publication that the alkyl esters of above mentioned acids would be suitable as fragrances.

Finally it is known from Dutch patent application 76,03354 that exo-2-bicyclo[2.2.1]heptyl-acetic acid esters are suitable as fragrances having a fruity and flowery odor. The esters according to the invention distinguish themselves therefrom by not only a chemical structure which is clearly different but also by a total different odor in which the character of conifers dominates.

The esters according to the invntion can be prepared according to methods known per se for flowery compounds by esterifying the corresponding acids. These acids can be prepared as described in the above mentioned references in Monatsh. Chem.Ber.

In Monatsh. Chem. 107 (1976) 387–94 the preparation of 6.6-dimethyl-bicyclo[2.2.1]hept-2-en-5-yl-methylketone is described, from which compound by oxidation with hypohalite the corresponding acid can be prepared. The corresponding dimethylbicycloheptane-acid may then be obtained by catalytic reduction. The 6-methyl and 6.6.-dimethyl-bicyclo[2.2.1]hept-2-en-5-carboxylic acids can be prepared by a Diels-Alder-reaction between cyclopentadiene and betamethacryl- respectively beta,beta-dimethylacrylylchloride, followed by hydrolysis and esterification. This method is described in Chem.Ber. 93 (1960) 2271–81.

In Dutch patent application 78,10966 is described how by means of oxidation of camphene with hydrogen peroxide a mixture of about 80% endo- and 20% exo-3.3-dimethylbicyclo[2.2.1]heptane-2-carboxylic acid can be obtained. Also by means of the other above mentioned methods mixtures of endo- and exo-acid are obtained, which can be separated into the individual components according to methods known per se for instance via the iodolactone, as described in Chem. Ber. 90 (1957) 1830–37. However, it is very advantageous to use the mixtures of endo- and exo-esters as a fragrance because these mixtures are also very suitable for this aim without further separation.

As already mentioned the esters according to the invention are powerful fragrances having a very natural odor reminiscent of conifers. For instance methyl-3.3-dimethyl-bicyclo[2.2.1]heptane-2-carboxylate has an odor especially reminiscent of pines with a clear rosemary note and a somewhat fruity nuance. The corresponding isopropyl- and propylester also have a piney odor but with a somewhat bloomy nuance. The allylester has besides the piney odor an olibanumlike note. The odor of the isobutylester does remember to cedar wood. The methyl- and ethylester of 3-methyl-bicyclo[2.2.1]heptane-2-carboxylic acid and the methylester of 6.6-dimethyl-bicyclo[2.2.1]hept-2-en-5-carboxylic acid do have a somewhat minty odor strongly resembling cedarleaf oil with tagetas-like and fruity notes. However, the ethyl- and isopropylester of last mentioned acid do have again a piney odor whereby the ethylester also has minty and the isopropylester flowery (muguet) and spicy nuances. The ethylester of 6-methyl-bicyclo[2.2.1]hept-2-en-5-carboxylic acid has a conifer-woody odor with floral nuances.

The esters according to the invention can be used successfully in perfume compositions or also as such as odor imparting agent. By their stability these esters are very suitable for perfuming of for instance soaps, washing and cleaning agents. In particular the saturated esters are also very stabile in oxidative mediums like modern detergents.

The phrase "perfume composition" is used to mean a mixture of fragrance and optionally auxiliary substances that may be dissolved in an appropriate solvent or mixed with a powdery substrate used to impart a desired odor to the skin and/or various products. Examples of said products are: soaps, washing agents, dish washing and cleaning agents, air refreshers and room sprays, pommanders, candles, cosmetics such as creams, colognes, pre- and after-shaving lotions, talcum powders, hair care agents, body deodorants and antiperspirants.

Fragrances and mixtures thereof which can be used for the preparation of perfume compositions are e.g. natural products such as essential oils, absolutes, resinoids, resins, concretes etc., synthetic fragrances, such as hydrocarbons, alcohols, aldehydes, ketones, ethers, acids, esters, acetals, ketals, nitrils etc., covering saturated and unsaturated compounds, aliphatic, carbocyclic and heterocyclic compounds.

Examples of fragrances to be used in combination with the compounds according to the invention are: geraniol, geranyl acetate, linalool, linalyl acetate, tetrahydrolinalool, citronellol, citronellyl acetate, myrcenol, myrcenyl acetate, dihydro myrcenol, dihydro myrcenyl acetate, tetrahydro myrcenol, terpineol, terpinyl acetate nopol, nopyl acetate, β-phenyl ethanol, β-phenylethyl acetate, benzyl alcohol, benzyl acetate, benzyl salicylate, benzyl benzoate, amyl salicylate, styrallyl acetate, dimethylbenzyl carbinol, trichloro methylphenylcarbinyl acetate, p-tert.butyl cyclohexyl acetate, isononyl acetate, vetiveryl acetate, vetiverol, α-hexyl cinnamon aldehyde, 2-methyl-3-(p-tert.butyl-phenyl)-propanol, 2-methyl-3-(p-isopropyl phenyl)-propanol, 3-p-tert.butylphenyl)-propanol, tricyclodecenyl acetate, tricyclodecenyl propionate, 4-(4-hydroxy-4-methylpentyl)-3-cyclohexane carbaldehyde, 4-(4-methyl-3-pentenyl)-3-cyclohexene carbaldehyde, 4-acetoxy-3-pentyl-tetrahydro pyran, 3-carboxymethyl-2-pentylcyclopentane, 2-n-heptyl cyclopentanone, 3-methyl-2-pentyl-2-cyclopentanone, n-decanal, n-dodecanal, 9-decenol-1, phenoxyethyl isobutyrate, phenyl acetaldehyde dimethylacetal, phenyl acetaldehyde diethylacetal, geranyl nitril, citronellyl nitril, cedryl acetate, 3-isocamphyl cyclohexanol, cedrylmethyl ether, isolongifolanon, aubepine nitrile, aubepine, heliotropine, coumarine, eugenol, vanilline, diphenyl oxide, hydroxy citronellal, ionones, methyl ionones, isomethyl ionones, irones, cis-3-hexenol and esters thereof, indan musk fragrances, tetraline musk fragrances, isochroman musk fragrances, macrocyclic ketones, macrolactone musk fragrances, ethylene brassylate, aromatic nitromusk fragrances.

Auxiliary agents and solvents that may be incorporated into perfume compositions according to the invention are e.g. ethanol, isopropanol, diethyleneglycol monoethylether, diethyl phtalate etc.

The amount of the esters that can be used in a perfume composition or in a perfumed product can be varied within broad limits and depends e.g. on the product wherein the perfume is used, the nature and the amount of the further components of the perfume compositions and the odor effect desired. Therefore, it is only possible to indicate very rough limits, which give, however, a person skilled in the art sufficient information concerning the odor strength and possibilities for the use of camphenic acid. In most cases a quantity of only 0.1% in a perfume composition is sufficient to obtain a clearly observable odor effect.

In products perfumed with the aid of perfume compositions according to the invention the concentration is lower and depends on the quantity of the composition used in the product. In some cases, however, concentrations of 30% are usable in the compositions to impart specific odor effects.

The following examples only illustrate the preparation and the use of the esters and do not restrict the invention thereto.

EXAMPLE I

Preparation of a mixture of methylesters of endo- and exo-3.3-dimethyl-bicyclo[2.2.1]-heptane-carboxylic acid.

A mixture of 27.2 g camphene and 30 g ethylformiate is refluxed. During several hours carefully 30 g 60%'s hydrogenperoxide is added dropwise with continuous agitation. Subsequently the mixture is stirred another 2.5 hours. Then the solvent is distilled off at atmospheric pressure. 20 g Toluene is added to the residue, the water layer is separated and the organic layer is washed twice with water. Then 40 g 20%'s sodiumhydroxide solution is added with Vigorous stirring whereafter the mixture is boiled for another hour. The water layer is separated, acidified with concentrated hydrochloric acid to pH 1 and extracted twice with toluene. The toluene layer is washed with water and then evaporated under reduced pressure.

Preparation of the methylesters.

From the above obtained mixture of acids the methylesters are prepared by adding 60 ml methanol and 8 g concentrated sulphuric acid. The reaction mixture is reflexed under agitation during 3.5 hours. Then about 40 ml methanol is distilled off and the residue is mixed with 20 ml toluene. This solution is subsequently washed with two times 20 ml water, 10 ml 5%'s soda solution and again 10 ml water. The solution is then evaporated under reduced pressure and the residue is distilled under reduced pressure: boiling point 80°–83° C./0.4 kPa.

Yield: 80%, calculated on the used acid. $n_D^{22} = 1.4668$.

EXAMPLE II

Preparation of a mixture of propylesters of the dimethylbicycloheptane-carboxylic acids.

To 20 g of the mixture of acids obtained according to the first part of example I 60 g n-propanol and 4 g concentrated sulphuric acid are added. The mixture is refluxed 3 hours after which the formed water is distilled off azeotropically. The residue is mixed with 20 ml toluene, washed twice with water, once with 5%'s soda-solution and again once with water. The solution is evaporated and the residue is distilled under reduced pressure.

Boiling point: 123°–128° C./2 kPa, yield 40%. $n_D^{22} = 1.4641$.

EXAMPLE III

Preparation of the mixture of isobutylesters of the dimethyl-bicycloheptane-carboxylic acids.

The isobutylesters are prepared in the way according to example II from 20 g of the mixture of acids and 60 ml isobutanol.

Boiling point: 92°–94° C./0.2 kPa, yield: 30%, $n_D^{22} = 1.4616$.

EXAMPLE IV

Preparation of a mixture of isopropylesters of the dimethylbicycloheptane-carboxylic acids.

20 g Of the mixture of acids according to example I, 60 g isopropanol and 4 g concentrated sulphuric acid are refluxed 7 hours. Then the water is distilled off azeotropically and the residue is treated in a way described in example II.

Boiling point: 70°–75° C./0.2 kPa. Yield: 23%. $n_D^{22} = 1.4600$.

EXAMPLE V

Preparation of a mixture of methylesters of endo- and exo-6.6-dimethyl-bicyclo[2.2.1]hept-2-en-5-carboxylic acid.

300 g Dicyclopentadiene is heated to 150° C. whereafter in 50 minutes 100 g β,β-dimethylacrylylchloride are added. Subsequently the mixture is refluxed another 10 hours at 150° C. The mixture is then distilled under reduced pressure whereby the unreacted starting material is removed and finally at 100°–130° C./0.7 kPa the wanted bicycloheptene-carboxylic acid chloride distills over; yield: 129 g.

The acid chloride is hydrolyzed by adding it during 30 minutes to a solution of 80 g NaOH in 300 ml water, the temperature rises to about 60° C. The mixture is agitated during another hour and refluxed. After the mixture is cooled it is extracted twice with cyclohexane. Then the water layer is acidified to pH 1 with 25%'s-sulphuric acid and again extracted twice with cyclohexane. The cyclohexane layer is evaporated and the residue obtained is distilled under reduced pressure. The yield is 47 g dimethylbicycloheptene-carbocyclic acid; boiling point: 110°–120° C./0.4 kPa.

25 g Sulphuric acid are added in 30 minutes to a mixture of the above obtained acid and 150 ml methanol whereby the temperature rises to about 45° C. The mixture is refluxed another 1.5 hours under agitation. Then the methanol is evaporated and the residue is mixed with cyclohexane. This solution is washed neutral with a Na₂CO₃-solution and washed once with water. The cyclohexane is then evaporated and the residue is distilled under reduced pressure. Yield: 29 g of the wanted methylesters (76%, calculated on the acid); boiling point: 75° C./0.7 kPa. $n_D^{22} = 1.4830$.

The ethylesters and isopropylesters were prepared in similar way, using the above mentioned mixture of acids and ethanol respectively isopropanol as starting components.

EXAMPLE VI

Preparation of 6-methyl-bicyclo[2.2.1]hept-2-en-5-carboxylic acid-ethylesters.

148 g Ethylcrotonate is heated at about 65° C. whereafter 115 g cyclopentadiene are added in two hours. The temperature rises to about 120° C. The mixture is stirred another 4 hours at this temperature. Then the reaction mixture is distilled under reduced pressure, obtaining 114 g of the wanted mixture of esters; boiling point: 66°–76° C./7 kPa; $n_D^{22} = 1.4413$.

EXAMPLE VII

Preparation of 3-methyl-bicyclo[2.2.1]heptane-2-carboxylic acid-ethylesters.

10 g Of the mixture of esters obtained according to example IV is dissolved in 100 ml absolute ethanol whereafter 100 mg hydrogenation catalyst (5% Pd of carbon) are added. Then the mixture is hydrogenated at atmospheric pressure till the theoretical quantity of hydrogen is taken up. Subsequently the catalyst is filtrated off, the ethanol evaporated and the residue distilled under reduced pressure; the yield of saturated ethylesters is 90%; $n_D^{20} = 1.4581$.

EXAMPLE VIII

A perfume composition of the "piney type" is prepared according to the following recipe:

|  | Parts by weight |
|---|---|
| "Mousse de chêne absolue" Jugoslavian | 5 |
| Rosemary oil French | 20 |
| Bornyl acetate | 557 |
| Pine needles oil Jugoslavian | 40 |
| Cedar wood oil Virginia | 50 |
| Methyl-nonyl-acetaldehyde | 10 |
| 6-acetyl-1-isopropyl-2.3.3.5-tetramethylindan+ | 5 |
| 4-acetoxy-3-pentyl-tetrahydropyran | 50 |
| 2.4-dimethyl-cyclohex-3-ene-carbaldehyde | 10 |
| Allyl-(3-methylbutoxy)-acetate | 3 |
| Cedrylmethylether | 3 |
| Dodecanal | 2 |
| Sage-oil Jugoslavian | 5 |
| Terpineol | 150 |
| Galbanum resinoide | 20 |
| 2-(3-heptyl)-1.3-dioxolan | 20 |
| Methylester mixture according to example I | 50 |
|  | 1000 |

+according to Dutch patent application 78,02038.

EXAMPLE IX

A perfume composition of the "Cedar type" for use in room sprays prepared according to the following recipe:

|  | Parts by weight |
|---|---|
| Borneol | 20 |
| Ethylmaltol | 2 |
| Bornylacetate | 366 |
| Pine needles oil Jugoslavian | 60 |
| Cedar-wood oil Virginia | 50 |
| Methyl-nonyl-acetaldehyde | 15 |
| 6-acetyl-1-isopropyl-2.3.3.5-tetramethylindan | 10 |
| 4-acetoxy-3-pentyl-tetrahydropyran | 30 |
| Cedrylmethylether | 10 |
| Appelbase A 119550[1] | 200 |
| Cedar-wood terpenes Texas | 200 |
| Tricyclo [5.2.1.0^{2.6}]decenyl acetate | 50 |
| Dihydromyrcenol | 50 |
| Litsea Cubeba oil | 10 |
| Patchouly oil | 15 |

| | Parts by weight |
|---|---|
| Curgix P[2] | 5 |
| Aubepine ex p-cresol | 10 |
| Turpentine-oil Portuguese | 160 |
| Cinnamic aldehyde | 2 |
| Isononylaldehyde | 10 |
| 2.4-dimethyl-cyclohex-3-ene-carbaldehyde | 25 |
| Propylester mixture according to example II | 100 |
| | 1400 |

[1]Fragrance base, put upon the market by Naarden International N.V.
[2]Fragrance base, put upon the market by Antoine Chiris, Grasse France.

A room spray may be prepared by mixing 27.2 g anhydrous ethanol, 2 g propylene glycol, 4.8 g diethylene glycol and 166 g freon with 1.2 of above mentioned perfume composition. Aerosol bombs were filled with this mixture.

EXAMPLE X

A perfume composition of the "conifer-type" is prepared according to the following recipe:

| | Parts by weight |
|---|---|
| Coumarin | 10 |
| Diphenyloxide | 10 |
| Benzyl acetate | 60 |
| Olibanum resinoide | 60 |
| Galbanum resinoide | 10 |
| Myrcenyl acetate | 80 |
| Methyl-nonylacetaldehyde | 30 |
| Dodecanal | 5 |
| Lavendel oil French | 50 |
| Cedar-wood oil Virginia | 50 |
| Alfa pinene | 100 |
| Methylidihydrojasmonate | 5 |
| 2.4-dimethyl-cyclohex-3-ene-carbaldehyde | 5 |
| Bornyl acetate | 505 |
| Methylester mixture according to example V | 20 |
| | 1000 |

We claim:

1. A perfume composition comprising one or more esters of methyl substituted bicyclo[2.2.1]heptane- and/or heptene-carboxylic acid having the following formulae:

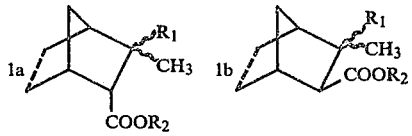

ENDO      EXO wherein the dotted line is a single or double bond; $R_1$ is selected from a group consisting of $CH_3$ and H; and $R_2$ is selected from a group consisting of alkyl and alkenyl having 1–4 carbon atoms.

2. The perfume composition as described in claim 1, wherein $R_1$ is $CH_3$ and $R_2$ is selected from a group consisting of alkyl having one to four carbon atoms and alkenyl having one to four carbon atoms.

3. The perfume composition as described in claim 1, wherein $R_1$ is $CH_3$ and $R_2$ is selected from a group consisting of alkyl having one to four carbon atoms.

4. The perfume composition as described in claim 1 wherein $R_1$ is $CH_3$ and $R_2$ is selected from a group consisting of alkenyl having one to four carbon atoms.

5. The perfume composition as described in claim 1, wherein $R_1$ is $CH_3$ and $R_2$ is an allyl group.

6. The perfume composition as described in claim 1, wherein $R_1$ is H and $R_2$ is selected from a group consisting of alkyl having one to four carbon atoms.

7. The perfume composition according to claim 1, containing at least 0.1% by weight of the esters.

8. Perfumed articles containing the perfume compositions as described in claim 1.

UNITED STATES PATENT AND TRADEMARK OFFICE
CERTIFICATE OF CORRECTION

PATENT NO. : 4,442,025
DATED : April 10, 1984
INVENTOR(S) : Harmannus Boelens, et al.

It is certified that error appears in the above-identified patent and that said Letters Patent is hereby corrected as shown below:

First page, 4th line of Item 54, "HEPTENE" should read --HEPTANE--;

First page, 5th line of Item 54, "HEPTINE" should read --HEPTENE--;

Col. 1, line 21, "]2.2.1]" should read --[2.2.1]--;

Col. 2, line 16, after "reminiscent" insert --of--;

Col. 2, line 30, "flowery" should read --analogous--;

Col. 3, line 44, before "nopol" insert a comma;

Col. 3, line 52, "3-p-tert." should read --3-(p-tert.--;

Col. 7, line 41, "Methylidihydrojasmonate" should read --Methyldihydrojasmonate--.

Signed and Sealed this

Thirtieth Day of October 1984

[SEAL]

Attest:

GERALD J. MOSSINGHOFF

Attesting Officer

Commissioner of Patents and Trademarks